United States Patent [19]
Bonnet

[11] Patent Number: 5,135,524
[45] Date of Patent: Aug. 4, 1992

[54] RESECTOSCOPE

[75] Inventor: Ludwig Bonnet, Knittlingen, Fed. Rep. of Germany

[73] Assignee: Richard Wolf GmbH, Knittlingen, Fed. Rep. of Germany

[21] Appl. No.: 525,517

[22] Filed: May 18, 1990

[30] Foreign Application Priority Data

Jun. 27, 1989 [DE]  Fed. Rep. of Germany ....... 3921000

[51] Int. Cl.⁵ .............................................. A61B 17/36
[52] U.S. Cl. ..................................................... 606/46
[58] Field of Search .................... 606/46, 41, 45, 47

[56] References Cited

U.S. PATENT DOCUMENTS

| | | | |
|---|---|---|---|
| 3,850,175 | 11/1974 | Iglesias | 606/46 |
| 4,068,667 | 1/1978 | Iglesias | 606/46 |
| 4,132,227 | 1/1979 | Ibe | 128/4 |
| 4,657,018 | 4/1987 | Hakky | 606/46 |

FOREIGN PATENT DOCUMENTS

| | | |
|---|---|---|
| 2617556 | 11/1976 | Fed. Rep. of Germany . |
| 7626244 | 8/1977 | Fed. Rep. of Germany . |
| 2637747 | 2/1978 | Fed. Rep. of Germany . |
| 2002236 | 2/1979 | United Kingdom . |

*Primary Examiner*—Max Hindenburg
*Attorney, Agent, or Firm*—Panitch Schwarze Jacobs & Nadel

[57] ABSTRACT

In a resectoscope, the inner barrel situated in the outer barrel, of the resectoscope is provided at the distal end, which projects beyond the outer barrel, with an insulating element to strengthen it, which element is provided in its outer surface for the length of an enlargement of the outer barrel with a part-cylindrical recess which produces at the distal end an enlarged outlet space, to which the liquid from the bladder flows in sufficient quantity via longitudinal slots in the enlargement of the outer barrel and is then extracted at the proximal end of the barrels.

8 Claims, 1 Drawing Sheet

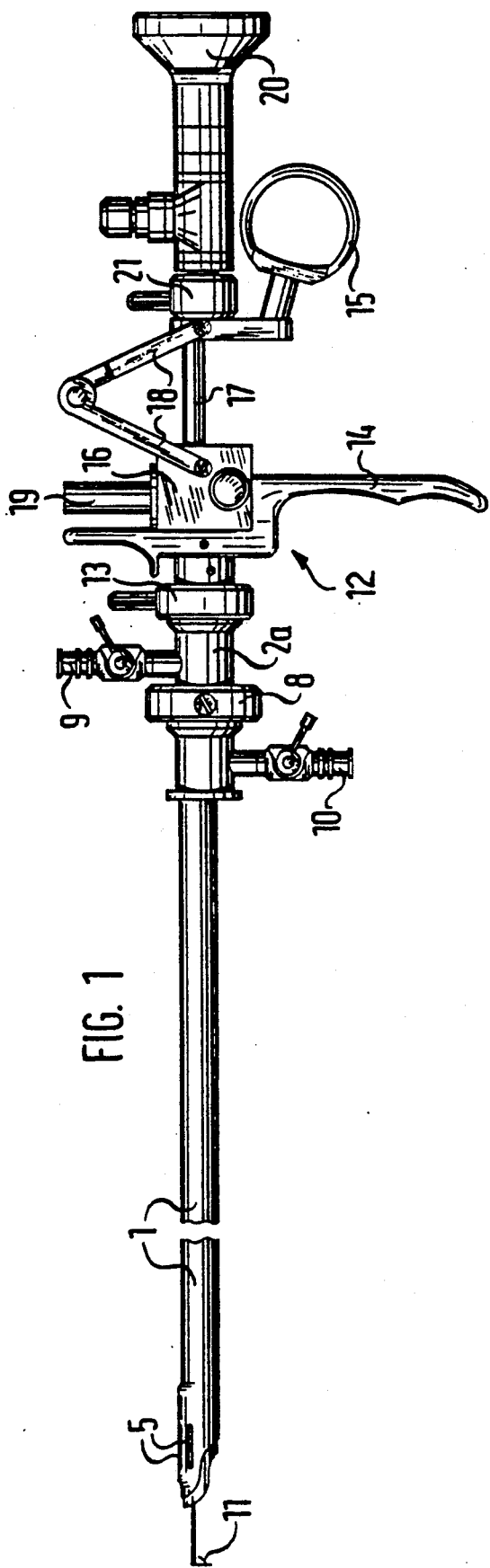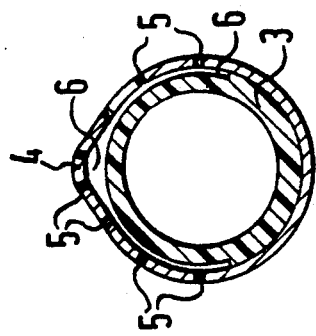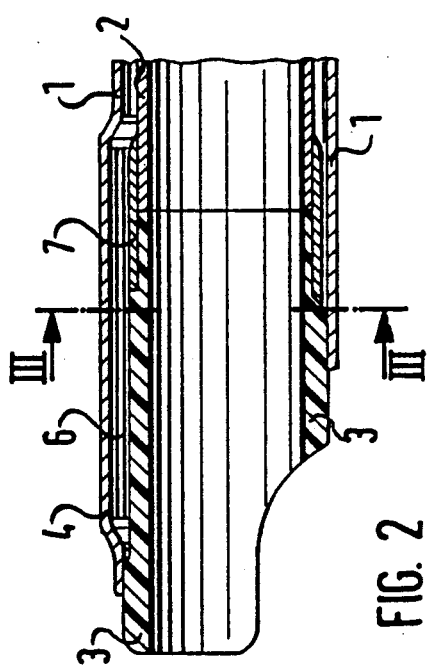
FIG. 1
FIG. 3
FIG. 2

RESECTOSCOPE

BACKGROUND OF THE INVENTION a) Field of the Invention

This invention relates to a resectoscope of the kind having an outer barrel and also an inner barrel formed as an insulating element at its distal end, to have passed through it a telescope and a means of supplying current to the distal resection loop, which means is displaceable by a carrier, the space left open in the inner barrel being used to feed an irrigating liquid into the bladder and the space between the inner and outer barrels being used to drain out the irrigating liquid through distal openings in the outer barrel.

b) Description of the Prior Art

Such resectoscopes are disclosed in DE-GM 7426959 U.S. Pat. No. 4,132,227, DE-GM 7626244 and DE-OS-2617556. To achieve an adequate circulation of irrigating liquid, these known resectoscopes have barrels of large cross-section, particularly at the distal end, which makes them more difficult to insert into the urethra and may even result in injury being caused to the mucous membrane of the urethra.

The main object of the present invention is, in resectoscopes of the above-mentioned kind, to provide a strong insulating element at the distal end of the inner barrel which will prevent current from being transmitted from the resection loop to the outer barrel, whilst at the same time providing adequate drainage for irrigant media from the bladder with the smallest possible cross-section for the outer barrel.

To this end, the present invention consists in a resectoscope having an outer barrel and having an inner barrel, formed as an insulating element at its distal end, to have passed through it a telescope and a means of supplying current to the distal resection loop, which means is displaceable by a carrier, the space left open in the inner barrel being used to feed an irrigating liquid into the bladder and the space between the inner and outer barrels being used to drain out the irrigating liquid through distal openings in the outer barrel, characterised in that the distal insulating element of the inner barrel is reduced in a diameter at the outer circumference in a part-cylindrical configuration providing a circumferential recess, over a length for which it is overlapped by the distal end of the outer barrel to form a space which is connected to slots for the outflow of irrigating liquid and to a closable connecting nozzle.

By achieving the object in this way, it is possible to insulate the resection loop satisfactorily from the barrel and the user of the resectoscope whilst making the distal end of the instrument strong enough for insertion in the urethra, and to obtain a sufficiently large space between the inner and outer barrels to allow the liquid to be drained out of the bladder even though the insulating element is strongly made.

The circumferential recess in the insulating element makes the space between the inner and outer barrels available and at the same time it keeps the cross-section of the resectoscope relatively small at the distal end.

In a preferred embodiment of the invention the proximal end of the insulating element whose diameter is reduced to that of the inner barrel is non-releasably connected to the distal end of the inner barrel by means of a cylindrical ring.

Advantageously, the insulating element has a cylindrical recess to receive the inner barrel.

BRIEF DESCRIPTION OF THE DRAWINGS

In order that the invention may be more readily understood, an embodiment thereof will now be described, by way of example, with reference to the accompanying drawings, in which:

FIG. 1 is a side elevation of an endoscope constructed according to the invention, FIG. 2 is a longitudinal section through a distal end of the resectoscope shown in FIG. 1 to an enlarged scale, but omitting a resection loop, and FIG. 3 is a cross-section on line III—III of FIG. 2.

DESCRIPTION OF THE PREFERRED EMBODIMENT

Referring to the drawings, a resectoscope comprises an outer barrel 1 and an inner barrel 2. Distally, the inner barrel 2 terminates in an insulating element 3 which projects beyond the distal end of the outer barrel. At the distal end and along the longitudinally directed top surface, the outer barrel is provided for a certain length with an enlargement or bulge 4 which has a plurality of longitudinal slots 5. For approximately half the length of the enlargement 4, the insulating element 3 is provided on its outer surface or circumference with a circumferential recess 6 which extends in a part-cylindrical configuration around the greater part of the circumference. Proximally the insulating element 3 butts against the distal end of the inner barrel 2 and is non-releasably connected thereto by a cylindrical ring 7.

The inner barrel 2 terminates proximally in an enlargement 2a which is sealed into the proximal end of the outer barrel 1 by a clamping ring 8 and which is provided with a shut-off cock 9 to allow an irrigating liquid to be fed into the interior of the inner barrel 2. The distal recess 6 between the outer barrel 1 and the insulating element 3 communicates in use with the bladder to be irrigated via the slots 5 and it terminates proximally in a shut-off cock 10 to allow the irrigating liquid fed into the bladder to be withdrawn.

For resection, an electrode carrier 12 which actuates the cutting loop 11 in the axial direction is inserted in the inner barrel 2, being releasably connected to the inner barrel 2 by a taper coupling and a clamping ring 13. The cutting movement of the cutting loop 11 is produced by moving part 14 of the handle towards its fixed part 15, which draws a block 16 back on guide 17 in opposition to the leg spring fitted to linkage 18. The cutting loop 11 is secured in block 16 in such a way that it can be exchanged and it is connected via an HF connection 19 to a current source.

The resection being performed is watched through a telescope, having an eyepiece 20, which extends through the inner barrel and which, once again, is held in place by a taper coupling and a clamping ring 21.

The insulating element 3 provides insulation between the two barrels 1 and 2 so as to prevent any transmission of current taking place from the cutting loop to the barrels.

Whilst a particular embodiment has been described, it should be appreciated that the invention is not limited thereto but includes all modifications and variations falling within its scope.

I claim:

1. A resectoscope comprising an outer barrel, an inner barrel positioned within the outer barrel, each of the inner barrel and the outer barrel having a proximal end and a distal end, the distal end of the outer barrel having an opening, the distal end of the inner barrel being formed as an insulating element, the insulating element having a reduced diameter section at an outer circumference thereof in a part-cylindrical configuration over a length in which the insulating element is overlapped by the distal end of the outer barrel, the inner barrel having a channel therethrough for feeding an irrigating liquid into a bladder of a patient and for passing a telescope and a distal resection loop which projects beyond the distal end of the inner barrer, the inner barrel and the outer barrel defining a second channel therebetween for removing the irrigating liquid from the bladder through the distal opening in the outer barrel.

2. A resectoscope according to claim 1, wherein the insulating element has a distal end and a proximal end, the proximal end having an outer diameter which is reduced as compared to the outer diameter of the distal end of the insulating element and is further reduced compared to the reduced diameter at the outer circumference of the insulating element in the part-cylindrical configuration, the proximal end of the insulating element being non-releasably connected to the distal end of the inner barrel by means of a cylindrical ring.

3. A resectoscope according to claim 2, wherein the ring is a separate ring element non-releasably connecting the proximal end of the insulating element to the distal end of the inner barrel.

4. A resectoscope according to claim 3, wherein the separate ring element has an inner diameter corresponding both to the further reduced outer diameter of the proximal end of the insulating element and to the outer diameter of the distal end of the inner barrel.

5. A resectoscope according to claim 4, wherein the separate ring element has an outer diameter corresponding to the reduced outer diameter of the insulating element in the part-cylindrical configuration.

6. A resectoscope according to claim 1, wherein the insulating element has a cylindrical recess for receiving the inner barrel.

7. A resectoscope according to claim 1, wherein the outer circumference of the distal insulating element is reduced in diameter in a part-cylindrical configuration, wherein the part-cylindrical configuration is greater than half the outer circumference.

8. A resectoscope according to claim 1 wherein said opening in the distal end of the outer barrel comprises longitudinal slots which overlie a portion of the reduced diameter section.

* * * * *